United States Patent [19]

Schmerling

[11] B 3,992,451

[45] Nov. 16, 1976

[54] PREPARATION OF KETONES

[75] Inventor: Louis Schmerling, Riverside, Ill.

[73] Assignee: Universal Oil Products Company, Des Plaines, Ill.

[22] Filed: Jan. 31, 1974

[21] Appl. No.: 438,484

[44] Published under the second Trial Voluntary Protest Program on February 17, 1976 as document No. B 438,484.

Related U.S. Application Data

[63] Continuation-in-part of Ser. No. 212,753, Dec. 27, 1971, abandoned.

[52] U.S. Cl.............................. 260/586 C; 260/592; 260/593 R; 260/597 T
[51] Int. Cl.².................................... C07C 45/02
[58] Field of Search............ 260/586 R, 586 C, 592, 260/590, 593 R, 597 T

[56] References Cited
UNITED STATES PATENTS

| | | | |
|---|---|---|---|
| 2,495,286 | 1/1950 | Brubaker.......................... | 260/597 T |
| 2,562,393 | 7/1951 | Reppe............................. | 260/586 C |
| 3,790,643 | 2/1974 | Anderson et al................ | 260/586 R |

*Primary Examiner*—Norman Morgenstern
*Attorney, Agent, or Firm*—James R. Hoatson, Jr.; Raymond H. Nelson; William H. Page, II

[57] ABSTRACT

Saturated ketones are prepared by reacting a saturated or alkylaramatic hydrocarbon with an olefinic hydrocarbon in the presence of carbon monoxide, a hydrogen chloride compound and a catalyst consisting essentially of an organic peroxide at a temperature at least as high as the decomposition temperature of said peroxide.

10 Claims, No Drawings

PREPARATION OF KETONES

CROSS-REFERENCE TO RELATED APPLICATIONS

This application is a continuation-in-part of copending application Ser. No. 212,753 filed Dec. 27, 1971, now abandoned, the contents of said copending application being incorporated herein by reference.

BACKGROUND OF THE INVENTION

The prior art has shown the synthesis of oxygen-containing compounds by utilizing certain catalytic compositions of matter in the presence of carbon monoxide. For example, it has been shown that a Friedel-Crafts synthesis of aldehydes may be accomplished by the condensation of carbon monoxide with a saturated hydrocarbon in the presence of anhydrous aluminum chloride. Likewise, the prior art has also shown that ketones may be prepared from aldehydes and olefins using a peroxide-initiated reaction. However, in the aforementioned formation of aldehydes from carbon monoxide and a saturated hydrocarbon, the catalyst which is used is anhydrous aluminum chloride which catalyzes ionic reactions and, if hydrogen chloride is present in the reaction mixture, it must be in an anhydrous condition.

In contradistinction to the prior art, I have now discovered that when an organic peroxide is decomposed in the presence of a saturated hydrocarbon, an olefin, carbon monoxide, and hydrogen chloride (aqueous or anhydrous), a carbonyl free radical is formed which adds to carbon monoxide and the olefinic hydrocarbon to produce an intermediate which rapidly extracts hydrogen from hydrogen chloride to produce a ketone. The aforementioned reaction involves the condensation of only one or two olefin molecules. As will hereinafter be shown in greater detail, when the reaction is effected in the absence of hydrogen chloride, telomerization, which is akin to polymerization, of the olefin occurs yielding a high molecular weight polymeric product. The mechanism by whcih the hydrogen chloride compound is involved is illustrated by the following equations:

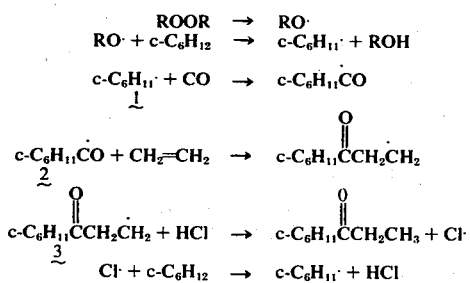

The cyclohexyl radical formed in the last step starts a new cycle.

In the absence of hydrogen chloride, telomerization occurs. The cyclohexyl radical (1) or the carbonyl radical (2) reacts with many molecules of olefin.

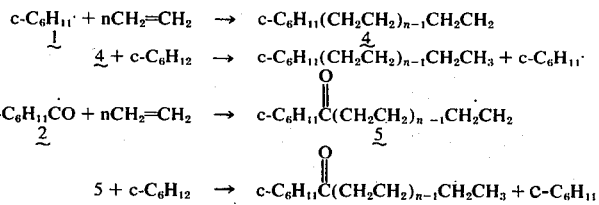

$n = 2–20$ or more.

This reaction utilizing an organic peroxide and hydrogen chloride can be accomplished regardless of whether the hydrogen chloride is in an anhydrous or aqueous state.

This invention relates to a process for the preparation of useful compounds and particularly to a process for the preparation of saturated ketones. More specifically the invention is concerned with the reaction of saturated hydrocarbons with olefinic hydrocarbons in the presence of certain additives whereby a liquid saturated ketone may be produced. Oxygen-containing compounds, and particularly ketones, will find a wide variety of uses in the chemical field. As an example of these uses, it is pointed out that ethyl butyl ketone which may be produced according to the process of the present invention by reacting a butane and ethylene in the presence of certain catalysts and other additives of the type hereinafter set forth in greater detail is used in solvent mixtures for air-drying and chemical finishes as well as being an intermediate in the preparation of polyvinyl and nitrocellulose resins.

It is therefore an object of this invention to provide a process for preparing oxygen-containing saturated compounds.

A further object of this invention is to provide a process for preparing oxygen-containing compounds such as ketones by reacting saturated hydrocarbons with olefinic hydrocarbons in the presence of carbon monoxide and a catalyst of the type hereinafter set forth in greater detail.

In one aspect an embodiment of this invention resides in a process for the preparation of a ketone which comprises reacting a saturated or alkylaromatic hydrocarbon with an olefinic hydrocarbon in the presence of carbon monoxide, a hydrogen chloride compound and a catalyst consisting essentially of an organic peroxide at free radical-generating conditions, and recovering the resultant ketone.

A specific embodiment of this invention is found in a process for preparing a ketone which comprises reacting cyclohexane with ethylene in the presence of carbon monoxide, hydrochloric acid and a catalyst comprising di-t-butyl peroxide at a temperature at least as high as the decomposition temperature of said di-t-butyl peroxide and recovering the resultant ethyl cyclohexyl ketone.

Other objects and embodiments will be found in the following further detailed description of the present invention.

As hereinbefore set forth the present invention is concerned with a process for preparing oxygen-containing saturated compounds, and particularly ketones.

The desired products are obtained by reacting a saturated hydrocarbon in the presence of carbon monoxide and a catalyst comprising a free radical-generating compound, preferably an organic peroxide. In addition, it has also been discovered that the presence of a promoter such as acidic compounds of the type hereinafter set forth in greater detail will permit the recovery of the desired product in increased yields over the yields which are normally obtained without the presence of said promoter. The absence of said promoter will result in the obtention of polymeric compounds of relatively high molecular weight and not the relatively low weight ketones which comprise the desired product.

Suitable saturated hydrocarbons which may be utilized as one of the starting materials and reacted with the olefinic hydrocarbons in the presence of carbon monoxide and an acidic promoter according to the process of this invention will include paraffins, both normal and branched chain in configuration, and cycloparaffins. In the preferred embodiment of the invention, the paraffins and cycloparaffins will preferably contain at least 3 carbon atoms and will usually contain from about 3 to about 12 carbon atoms, the cycloparaffins will contain from about 5 to about 8 carbon atoms in the ring as well as lower alkyl substituted cycloalkanes in which the alkyl substituent will contain from 1 to about 5 carbon atoms and the cycloalkane will contain from about 5 to about 8 carbon atoms in the ring. Some specific examples of these saturated hydrocarbons which may be used will include propane, n-butane, isobutane, n-pentane, isopentane, n-hexane, n-heptane, n-octane, n-nonane, n-decane, n-undecane, n-dodecane, 2-methylpentane, 3-methylpentane, the isomeric methylhexanes, methylheptanes, methyloctanes, methylnonanes, methyldecanes, methylundecanes, 2,2-dimethylpentane, 2,2-dimethylbutane, 3,3-dimethylpentane, the isomeric dimethylhexanes, dimethylheptanes, gem-dimethyloctanes, gem-dimethylnonanes, gem-dimethyldecanes, 2,3-dimethylpentane, 2,3-dimethylhexane, 2,3-dimethylheptane, 2,3-dimethyloctane, 2,3-dimethylnonane, 2,3-dimethyldecane, as well as isomers of these alkanes such as ethylhexanes, ethylheptanes, ethyloctanes, 2,3-diethylpentane, 2,3-diethylhexane, 2,3-diethylheptane, 2,3-diethyloctane, etc., cyclopentane, cyclohexane, cycloheptane, cyclooctane, methylcyclopentane, methylcyclohexane, methylcycloheptane, ethylcyclopentane, ethylcyclohexane, ethylcycloheptane, ethylcyclooctane, n- and isopropylcyclopentane, n- and isopropylcyclohexane, n- and isopropylcycloheptane, n- and isopropylcyclooctane, pentylcyclopentanes, pentylcyclohexanes, pentylcycloheptanes, pentylcyclooctanes, 1,2-dimethylcyclopentane, 1,2-dimethylcyclohexane, 1,2-dimethylcycloheptane, etc. It is to be understood that the aforementioned saturated hydrocarbons are only representative of the class of compounds which may be employed as starting materials and that the present invention is not necessarily limited thereto. In addition, it is also contemplated within the scope of this invention that alkyl substituted aromatic hydrocarbons may also be employed as one of the starting materials in the process of the present invention. Some specific examples of these alkyl substituted aromatic hydrocarbons in which the alkyl substituent is of the lower alkyl variety and will contain from 1 to about 5 carbon atoms which may be employed will include toluene, ethylbenzene, n-propylbenzene, iso-propylbenzene (cumene), n-butylbenzene, sec-butylbenzene, n-pentylbenzene, sec-pentylbenzene, 1-methylnaphthalene, 2-methylnaphthalene, 1-ethylnaphthalene, 2-ethylnaphthalene, 1-n-propylnaphthalene, 2-n-propylnaphthalene, 1-isopropylnaphthalene, 2-isopropylnaphthalene, 1-n-butylnaphthalene, 1-sec-butylnaphthalene, etc., the preferred alkylaromatic hydrocarbon being that which contains at least one hydrogen atom attached to the carbon atom of the alkyl substituent which is attached to the aromatic nucleus.

Olefinic hydrocarbons which may be reacted with the aforementioned saturated hydrocarbons in the process of the present invention will include olefins containing from 2 up to about 10 carbon atoms, being both straight chain, branched chain and cyclic in configuration, the preferred olefinic hydrocarbons being those which are designated as 1-alkenes. Some representative examples of these olefins will include ethylene (the preferred alkene), propene, 1-butene, 1-pentene, 1-hexene, 1-heptene, 1-octene, 1-nonene, 1-decene as well as the isomers thereof such as 2-butene, 2-pentene, 2-hexene, 3-hexene, 2-heptene, 3-heptene, 2-octene, 3-octene, 4-octene, 2-nonene, 2-decene, 3-decene, 4-decene, etc., 2-methyl-1-butene, 2-methyl-1-pentene, 2-methyl-1-hexene, 2-methyl-1-heptene, 2-methyl-1-octene, 2-methyl-1-nonene, 2,3-dimethyl-1-pentene, 2,3-dimethyl-1-hexene, 2,3-dimethyl-1-heptene, 2,3-dimethyl-1-octene, etc., cyclopentene, cyclohexene, cycloheptene, etc. It is to be understood that, as in the case with the saturated hydrocarbons, the aforementioned olefinic hydrocarbons are only representative of the class of compounds which may be reacted with the saturated hydrocarbons, and that the present invention is not necessarily limited thereto.

The catalysts which may be used in the present process are those which are capable of forming free radicals under the reaction conditions. These include peroxy compounds containing the bivalent radical, —O—O—, which decompose to form free radicals which initiate the general reaction of the present invention and which are capable of inducing the reaction of the saturated hydrocarbon with carbon monoxide and the olefinic hydrocarbon. Examples of these catalysts include the persulfates, perborates, and percarbonates, of ammonium and of the alkali metals, and organic peroxy compounds. The organic peroxy compounds constitute a preferred class of catalysts for use in the invention and include peracetic acid, persuccinic acid, dimethyl peroxide, diethyl peroxide, dipropyl peroxide, di-t-butyl peroxide, butyryl peroxide, lauroyl peroxide, benzoyl peroxide, tetralin peroxide, urea peroxide, t-butyl perbenzoate, t-butyl hydroperoxide, methylcyclohexyl hydroperoxide, cumene hydroperoxide, diisopropylbenzyl hydroperoxide, etc. Mixtures of peroxy compound catalysts may be employed or the peroxy compound catalyst may be utilized in admixture with various diluents. Thus, organic peroxy compounds which are compounded commercially with various diluents which may be used include benzoyl peroxide compounded with calcium sulfate, benzoyl peroxide compounded with camphor, etc. Only catalytic amounts (less than stoichiometric amounts) need be used in the process.

The reaction of the present process involving the aforementioned starting materials is effected at elevated reaction temperatures which should be at least as high as the initial decomposition temperature of the free radical-generating catalyst, such as the peroxide compound, in order to liberate and form free radicals which promote the reaction. In selecting a particular reaction temperature for use in the process of the present invention, two considerations must be taken into account. First, sufficient energy by means of heat must be supplied to the reaction so that the reactants, namely saturated hydrocarbons and olefinic hydrocarbons, will be activated sufficiently for condensation to take place when free radicals are generated by the catalyst. Second, free radical-generating catalysts such as peroxy compounds, particularly organic peroxides, decompose at a measurable rate with time in a logarithmic function dependent upon temperature. This rate of decomposition can be and ordinarily is expressed as the half life of a peroxide at a particular temperature. For example the half life in hours for di-t-butyl peroxide is 17.5 hours at 125°C., 5.3 hours at 135°C., and 1.7 hours at 145°C. (calculated from data for the first 33% decomposition). A reaction system temperature must then be selected so that the free radical-generating catalyst decomposes smoothly with the generation of free radicals at a half life which is not too long. In other words, sufficient free radicals must be present to induce the present chain reaction to take place, these radicals must be formed at a temperature at which the reactants are in a suitably activated state for condensation. When the half life of the free radical-generating catalyst is greater than 20 hours, radicals are not generated at a sufficient rate to cause the reaction of the process of the present invention to go forward at a practical rate. Thus the reaction temperature may be within the range of from about 50° to about 300°C. and at least as high as the decomposition temperature of the catalyst, by which is meant a temperature such as the half life of the free radical-generating catalyst is not greater than 20 hours. Since the half life for each free radical-generating catalyst is different at different temperatures, the exact temperature to be utilized in a particular reaction will vary. However, persons skilled in the art are well acquainted with the half life vs. temperature data for different free radical-generating catalysts. Thus it is within the skill of one familiar with the art to select the particular temperature needed for any particular catalyst. However, the operating temperatures generally do not exceed the decomposition temperature of the catalyst by more than about 150°C. since free radical-generating catalysts decompose rapidly under such conditions. For example, when a free radical-generating catalyst such as t-butyl perbenzoate is used, having a decomposition temperature of approximately 115°C., the operating temperature of the process is from about 115° to about 265°C. When di-t-butyl peroxide having a decomposition temperature of about 130°C. is used, the process is run at a temperature ranging from about 130° to about 280°C. Higher reaction temperatures may be employed, but little advantage is gained if the temperature is more than the herinbefore mentioned 150°C. higher than the decomposition temperature of the catalyst. THe general effect of increasing the operating temperature is to accelerate the rate of the condensation reaction between the saturated hydrocarbon and the olefinic hydrocarbon. However, the increased rate of reaction is accompanied by certain amounts of decomposition. In addition to the elevated temperatures which are utilized, the reaction may also be effected at elevated pressures ranging from about 1 to about 100 atmospheres or more, the preferred operating pressure of the process being that which is required to maintain a substantial portion of the reactants in liquid phase. Pressure is not an important variable in the process of this invention. However, because of the low boiling points of some of the reactants, it is necessary to utilize pressure-withstanding equipment to insure liquid phase conditions. In batch type operations, it is often desirable to utilize pressure-withstanding equipment to charge the reactants and catalyst to the vessel and to pressure the vessel with 10 or 30 or 50 or more atmospheres with an inert gas such as nitrogen. This helps to insure the presence of liquid phase conditions. However, when the mole quantity of reactants is sufficient, the pressure which they themselves generate at the temperature utilized is sufficient to maintain the desired phase conditions. Furthermore, the concentration of the catalyst employed in this process may vary over a rather wide range but it is desirable to utilize low concentrations of catalysts such as from about 0.1% to about 10% of the total weight of the combined starting materials charged to the process. The reaction time may be within the range of from less than one minute to many hours, depending upon temperature and half life of the catalyst. Generally speaking, contact times of at least 10 minutes are preferred.

In addition to the carbon monoxide and catalysts of the type hereinbefore set forth in greater detail the condensation of the saturated hydrocarbon with the olefinic hydrocarbon is also effected in the presence of a hydrogen chloride compound. The hydrogen chloride compound may be present as anhydrous hydrogen chloride, as concentrated hydrochloric acid (37–38% hydrogen chloride) or as a dilute aqueous solution of hydrogen chloride, the hydrogen chloride being present in an amount of from about 10% to about 37% in said aqueous solution. The hydrogen chloride, whether in anhydrous or aqueous state, serves to provide a ready source of hydrogen for abstraction and therefore prevents continuous addition of the intermediate radicals to the olefin to form a high molecular weight compound which is usually present as a wax when formed in the absence of hydrogen chloride. The hydrogen chloride will give up the hydrogen at such a rate so as to prevent telomerization (a form of polymerization) of the olefin, the hydrogen chloride being unique in this effect inasmuch as other hydrogen halides such as hydrogen bromide and hydrogen iodide will not act in this manner. No other substance is known which shows the same effect as does hydrogen chloride. As will hereinafter be shown in greater detail, the amount of water which is present is not critical inasmuch as some molecular hydrogen chloride which is necessary for the reaction mechanism of the present process will be present regardless of whether said hydrogen chloride is present in an anhydrous state or in an aqueous state. This fact will be hereinafter shown in greater detail in the appended examples at the end of the specification.

The ratio of the various reactants such as the saturated hydrocarbon, the olefinic hydrocarbon and the carbon monoxide is not a critical factor and a ketone will be obtained if there is present some carbon monoxide, olefinic hydrocarbon and saturated hydrocarbon as well as some hydrogen chloride provided that the temperature of the reaction is at least as high as the decomposition temperature of the organic peroxide catalyst which is present as the reaction initiator. Therefore, in the preferred embodiment of the invention, the carbon monoxide which is utilized to form the ketone will be present in an amount of from about 0.1:1 to about 3:1 moles of carbon monoxide per mole of saturated hydrocarbon. There will also be present approximately equimolar amounts of the olefinic hydrocarbon and the carbon monoxide. However, small excesses of either the olefinic hydrocarbon or the carbon monoxide may be used. These excesses may be present so that the range of carbon monoxide to olefinic hydrocarbon may be from about 0.5:1 to about 2.0:1 moles of carbon monoxide per mole of olefinic hydrocarbon.

The process of this invention may be effected in any suitable manner and may comprise either a batch or continuous type operation. For example, when a batch type operation is used, a quantity of the saturated hydrocarbon, the catalyst and the hydrogen chloride compound are placed in an appropriate apparatus, for example, an autoclave of the rotating or mixing type. Following this the olefinic hydrocarbon, if in gaseous form, is charged to the reactor as is the carbon monoxide until the desired operating pressure has been reached. Alternatively, if the olefinic hydrocarbon is in liquid form, it is placed in the reactor along with the saturated hydrocarbon prior to the charging of the carbon monoxide thereto. The autoclave and contents are then heated to the desired operating temperature which is, as hereinbefore set forth, at least as high as the decomposition temperature of the free radical-generating compound which acts as the catalyst for the reaction, and preferably in a range of from the aforesaid decomposition temperature to about 150°C. higher than the decomposition temperature. Following completion of the desired residence time which may range in duration of from about 0.5 up to about 10 hours or more, heating is discontinued and the reactor allowed to return to room temperature. Upon reaching room temperature the excess pressure is discharged and the autoclave is opened. The reaction product is recovered therefrom and thereafter is subjected to conventional means of separation which may include washing, drying, extraction, fractional distillation, crystallization, etc. whereby the desired ketone is separated from any unreacted saturated hydrocarbon, olefinic hydrocarbon and/or undesirable side products which may have formed during the reaction.

It is also contemplated within the scope of this invention that the process for preparing a ketone may be effected in a continuous manner of operation. When such a type of operation is used the starting materials comprising the saturated hydrocarbon, the olefinic hydrocarbon, the free radical-generating compound which acts as the catalyst for the reaction, and the hydrogen chloride compound along with the carbon monoxide are charged to a reaction zone which is maintained at the proper operating conditions of temperature and pressure. The starting materials may, if so desired, be charged to the reactor through separate lines or admixed prior to entry into said reactor and charged thereto in a single stream or two or three streams. Upon completion of the desired residence time, the reactor effluent is continuously withdrawn and subjected to separation steps similar to those hereinbefore set forth whereby the desired ketone is separated from any unreacted starting material such as saturated hydrocarbon and olefinic hydrocarbon, the ketone being passed to storage while the unreacted materials are recycled to the reaction zone to form a portion of the feed stock thereof.

The following examples are given to illustrate the process of the present invention and, however, are not intended to limit the generally broad scope of the present invention in strict accordance therewith.

EXAMPLE I

To the glass liner of a rotating autoclave was added 96 grams (1.1 mole) of cyclohexane, 6 grams (0.04 mole) of di-t-butyl peroxide, and 47 grams of concentrated hydrochloric acid. Following this, ethylene was pressed in along with carbon monoxide until an initial operating pressure of 90 atmospheres was reached, said 90 atmospheres consisting of 60 atmospheres of carbon monoxide and 30 atmospheres of ethylene. The autoclave was then heated to a temperature of 130°C. and maintained in a range of from 130° to 140°C. for a period of 4 hours, the maximum pressure at this temperature reaching 100 atmospheres. At the end of the 4-hour period, heating was discontinued and the autoclave allowed to return to room temperature, the final pressure at room temperature being 70 atmospheres. The excess pressure was discharged, the autoclave was opened and the reaction mixture was recovered therefrom. The product which comprised 132 grams of an amber upper layer was recovered, water-washed and subjected to fractional distillation. The bottoms remaining after removal of the cyclohexane which comprised 19 grams of a yellow-amber liquid was analyzed by means of preparative gas-liquid chromatography followed by infrared analysis, said analysis disclosing the presence of ethyl cyclohexyl ketone. The ethyl cyclohexyl ketone was present in an amount of 9 grams, the remaining portion of the bottoms comprising other products such as ethylcyclohexane, chlorocyclohexane, etc.

EXAMPLE II

To illustrate the operability of anhydrous hydrogen chloride to act as a promoter in obtaining the desired ketones, another experiment was run in which 85 grams of cyclohexane was added to the glass liner of a rotating autoclave along with 6 grams of di-t-butyl peroxide. The autoclave was sealed and 5 atmospheres of anhydrous hydrogen chloride, 30 atmospheres of ethylene and 60 atmospheres of carbon monoxide were pressed in. The autoclave was then heated to a temperature of 130°C. and maintained in a range of from about 130°–140°C. for a period of 4 hours, the maximum pressure at this temperature reaching 124 atmospheres. At the end of the residence time, heating was discontinued and the autoclave was allowed to return to room temperature, the final pressure at room temperature being 64 atmospheres. The excess pressure was discharged, the autoclave was opened and the reaction mixture comprising 113 grams of an amber upper layer was recovered, water-washed and subjected to fractional distillation. There was recovered 7 grams of ethyl cyclohexyl ketone along with an additional amount of ethylcyclohexane and 6 grams of a relatively low molecular weight higher-boiling product consisting of butylcyclohexane, butyl cyclohexyl ketone and ethyl ethylcyclohexyl ketone.

EXAMPLE III

In this example 102 grams (1.2 mole) of cyclohexane and 6 grams (0.04 mole) of di-t-butyl peroxide along with 45 grams of an aqueous hydrochloric acid solution were placed in the glass liner of a rotating autoclave. Propene and carbon monoxide were charged to the reactor until an initial operating pressure of 90 atmospheres was reached. The autoclave was then heated to a temperature of 130°C. and maintained in a range of from 130°–140°C. for a period of 4 hours during which time the maximum pressure rose to 120 atmospheres. At the end of the 4-hour period, heating was discontinued and the autoclave allowed to return to room temperature, the final pressure at room temperature being 72 atmospheres. The excess pressure was discharged and the reaction product comprising 130 grams of an upper layer was recovered. This layer was water-washed and then subjected to fractional distillation and the bottoms comprising 17 grams of an amber liquid were subjected to preparative gas-liquid chromatography followed by instrumental analysis. Infrared and nuclear magnetic resonance confirmed the presence of 3 grams N-propyl cyclohexyl ketone with a small amount (0.7 grams) of isopropyl cyclohexyl ketone also being present.

EXAMPLE IV

To illustrate the necessity for the presence of a hydrogen chloride compound in the reaction mixture to bring about the desired reaction and also to prevent formation of undesirable products, another experiment was performed in which 85 grams of cyclohexane along with 6 grams of di-t-butyl peroxide were placed in the glass liner of a rotating autoclave, no hydrogen chloride compound being used. The autoclave was sealed and pressured to 90 atmospheres by adding 30 atmospheres of ethylene and 60 atmospheres of carbon monoxide. The autoclave was then heated to a temperature of 130°C. and maintained in a range of from 130°–140°C. for a period of 4 hours, the maximum pressure during this time reaching 110 atmospheres. At the end of the 4-hour period, heating was discontinued and the autoclave was allowed to return to room temperature, the final pressure at room temperature being 48 atmospheres. The autoclave was opened and the reaction product consisting of 100 grams of liquid and 27 grams of wax which was insoluble in the liquid product was recovered. The liquid product was subjected to fractional distillation and the desired fraction subjected to analysis by means of preparative gas-liquid chromatography and infrared. There was obtained only 0.04 grams of the desired product comprising ethyl cyclohexyl ketone and 1.5 grams of ethylcyclohexane. The chief product comprised 26 grams of high-boiling viscous liquid material and 27 grams of a wax.

EXAMPLE V

In this experiment the reaction was again run in the absence of any hydrogen chloride compound but in the presence of water. As in the above examples, 85 grams of cyclohexane, 40 grams of water and 6 grams of di-t-butyl peroxide were placed in the glass liner of a rotating autoclave. The autoclave was sealed following which 30 atmospheres of ethylene and 60 atmospheres of carbon monoxide were pressed into the reactor. The autoclave was again heated to a temperature of 130° and maintained in a range of from 130°–140°C. for a period of 4 hours, the maximum pressure at this temperature reaching 118 atmospheres. At the end of 4 hours, heating was discontinued and the autoclave was allowed to return to room temperature, the final pressure at room temperature being 50 atmospheres. The excess pressure was discharged, the autoclave was opened and the reaction product which comprised 125 grams of liquid and 36 grams of a wax which was insoluble in the liquid product was recovered. The liquid product was treated in a manner similar to that set forth in the above examples, there being obtained only a trace of the desired product, namely, ethyl cyclohexyl ketone, 4 grams of ethylcyclohexane along with 10 grams of higher-boiling liquid product, and 36 grams of wax.

It is therefore readily apparent from a comparison of Examples I and II with IV and V that the presence of a hydrogen chloride compound is essential in order to prevent polymerization (telomerization) of the olefinic hydrocarbon to form higher-boiling liquid products and waxes along with a concomitant recovery of a low or negligible yield of the desired product.

EXAMPLE VI

In this example another experiment was performed to show that negligible amounts, if any, of aldehydes are formed under conditions which yield ketones in the presence of olefins. To illustrate this fact, 75 grams of cyclohexane along with 26 grams of concentrated hydrochloric acid, 51 grams of water and 6 grams of di-t-butyl peroxide were charged to the glass liner of a rotating autoclave. The autoclave was sealed and 90 atmospheres of carbon monoxide was pressed in. As in the preceding experiments, the autoclave was then heated to a temperature of 130° C. and maintained in a range of from 130°–140° C. for a period of 4 hours, the maximum pressure at this temperature reaching 125 atmospheres. At the end of the residence period, heating was discontinued and the autoclave was allowed to return to room temperature. The final pressure when the autoclave reached room temperature was 82 atmospheres, this pressure being released and the autoclave opened. The reaction product which consisted of 154 grams of liquid was recovered and treated in a manner similar to that set forth in the above examples. Analysis of the bottoms showed that there was recovered 5 grams of a higher-boiling product which consisted of a very complex mixture. Gas chromatography of the mixture showed at least 8 major peaks and 5 minor peaks, with little or no cyclohexanecarboxaldehyde being present.

EXAMPLE VII

In this example a rotating autoclave which contains 6 grams of di-t-butyl peroxide and 45 grams of an aqueous hydrochloric acid solution is sealed, following which 66 grams (1.5 mole) of propane and 28 grams (1.0 mole) of ethylene are charged thereto along with a sufficient amount of carbon monoxide so that an initial operating pressure of 90 atmospheres is reached. The autoclave is then heated to a temperature of 130° C. and maintained in a range of from 130°–140° C. for a period of 4 hours. At the end of the 4-hour period, heating is discontinued and the autoclave is allowed to return to room temperature, the final pressure at room temperature being about 75 atmospheres. The excess pressure is discharged and the reaction product is recovered therefrom. After purification steps have been completed., the product is subjected to fractional distillation under reduced pressure and the bottoms which are recovered therefrom are analyzed by means of preparative gas-liquid chromatography, said analysis disclosing the presence of ethyl isopropyl ketone.

EXAMPLE VIII

A mixture consisting of 96 grams (1.1 mole) of cyclohexane, 56 grams (0.5 mole) of 1-octene along with 6 grams of benzoyl peroxide and 50 grams of an aqueous solution of hydrochloric acid is placed in the glass liner of a rotating autoclave. The autoclave is sealed and carbon monoxide is pressed in until an initial operating pressure of 90 atmospheres is reached. The autoclave is then heated to a temperature of 100° C. and maintained in a range of from 100°–110° C. for a period of 6 hours. At the end of the 6-hour period, heating is discontinued and the autoclave is allowed to return to room temperature. The excess pressure is thereafter discharged, the autoclave is opened and the reaction product is recovered therefrom. After purification steps and fractional distillation, the bottoms are analyzed by means of preparative gas-liquid chromatography, the presence of the desired product comprising n-octyl cyclohexyl ketone being established thereby.

EXAMPLE IX

To the glass liner of a rotating autoclave was charged 92 grams of p-xylene, 6 grams of di-t-butyl peroxide and 35 grams of aqueous concentrated hydrochloric acid. The autoclave was sealed following which 30 atmospheres of ethylene and 60 atmospheres of carbon monoxide were charged thereto so that an initial operating pressure of 90 atmospheres was reached. Thereafter the autoclave was heated to a temperature of 130° and maintained in a range of from 130°–140° C. for a period of 4 hours. Upon completion of the desired residence time, heating was discontinued, the autoclave was allowed to return to room temperature and a pressure of 75 atmospheres. The excess pressure was discharged. The autoclave was then opened and the reaction product was recovered therefrom. After treating the product with potassium carbonate, it was subjected to fractional distillation. Analysis of the bottoms by means of preparative gas-liquid chromatography and infrared analysis showed the presence of the desired product which comprised ethyl P-methylbenzyl ketone together with p-methyl-n-propylbenzene and p,p′-dimethylbibenzyl.

I claim as my invention:

1. A process for the preparation of a ketone which comprises reacting a hydrocarbon selected from the group consisting of saturated and alkylaromatic hydrocarbons with an olefinic hydrocarbon in the presence of carbon monoxide, anhydrous or aqueous hydrogen chloride and an organic peroxy free radical catalyst at a temperature at least as high as that necessary to generate free radicals, and recovering the resultant ketone.

2. The process of claim 1 in which said hydrocarbons are reacted under sufficient pressure to maintain a substantial portion of the hydrocarbons in liquid phase.

3. The process of claim 1 in which the firstmentioned hydrocarbon is a saturated hydrocarbon.

4. The process of claim 1 in which the firstmentioned hydrocarbon is an alkylaromatic hydrocarbon having an alkyl group of from 1 to about 5 carbon atoms.

5. The process as set forth in claim 1 in which said catalyst is di-t-butyl peroxide.

6. the process as set forth in claim 1 in which said catalyst is benzoyl peroxide.

7. The process as set forth in claim 3 in which said saturated hydrocarbon is cyclohexane, said olefinic hydrocarbon is ethylene and said ketone is ethyl cyclohexyl ketone.

8. The process as set forth in claim 3 in which said saturated hydrocarbon is cyclohexane, said olefinic hydrocarbon is propene and said ketone is n-propyl cyclohexyl ketone.

9. The process as set forth in claim 3 in which said saturated hydrocarbon is cyclohexane, said olefinic hydrocarbon is 1-octene and said ketone is n-octyl cyclohexyl ketone.

10. The process as set forth in claim 3 in which said saturated hydrocarbon is propane, said olefinic hydrocarbon is ethylene and said ketone is ethyl isopropyl ketone.

* * * * *